United States Patent [19]
Monteleone et al.

[11] Patent Number: 5,927,281
[45] Date of Patent: Jul. 27, 1999

[54] GOGGLES FOR PREVENTING EXPOSURE KERATITIS

[75] Inventors: Tamela A. Monteleone; Michael N. Monteleone, both of Murrieta, Calif.

[73] Assignee: The Board of Trustees of the Leland Stanford Junior University, Stanford, Calif.

[21] Appl. No.: 09/034,180

[22] Filed: Mar. 3, 1998

Related U.S. Application Data

[60] Provisional application No. 60/039,748, Mar. 3, 1997.
[51] Int. Cl.⁶ ........................................................ A61F 9/00
[52] U.S. Cl. ...................................... 128/858; 2/15; 2/426
[58] Field of Search ...................................... 128/857, 858; 2/15, 426, 427, 428, 431, 440, 454, 445

[56] References Cited

U.S. PATENT DOCUMENTS

| | | | |
|---|---|---|---|
| 3,010,109 | 11/1961 | Gray et al. | 2/14 |
| 4,051,557 | 10/1977 | Bengtson et al. | 2/430 |
| 4,122,847 | 10/1978 | Craig | 128/132 R |
| 4,348,775 | 9/1982 | Haslbeck | 2/452 |
| 4,429,956 | 2/1984 | Herbert | 350/410 |
| 4,461,303 | 7/1984 | Refojo et al. | 128/630 |
| 4,649,908 | 3/1987 | Ghaly | 128/132 R |

*Primary Examiner*—Michael A. Brown
*Attorney, Agent, or Firm*—Lumen Intellectual Property Services

[57] ABSTRACT

The invention presents goggles for preventing a patient from developing exposure keratitis. The goggles include first and second concave eyepieces which form chambers over the patient's eyes. The goggles also include an adjustable nose strap connecting the eyepieces and an adjustable head strap for securing the goggles to the patient. The first and second eyepieces have first and second holes, respectively. A first valve assembly is attached to the first eyepiece for regulating fluid flow through the first hole, and a second valve assembly is attached to the second eyepiece for regulating fluid flow through the second hole. Liquids such as artificial tears are instilled in each chamber through the valve assemblies to keep the patient's eyes moist. The goggles further include first and second cushioning members, preferably air bladders, attached to the rims of the eyepieces. The cushioning members seal the goggles to the patient's face while preventing the patient from developing skin damage or pressure sores.

15 Claims, 1 Drawing Sheet

GOGGLES FOR PREVENTING EXPOSURE KERATITIS

RELATED APPLICATION INFORMATION

This application claims priority from provisional application Ser. No. 60/039,748 filed Mar. 3, 1997.

FIELD OF THE INVENTION

The present invention relates generally to goggles, and in particular to goggles for preventing exposure keratitis.

DESCRIPTION OF PRIOR ART

Exposure keratitis and subsequent corneal ulceration is a recurrent problem for patients who are in intensive care units or under general anesthesia. Exposure keratitis is damage to the cornea which occurs when the eyes become dehydrated. Patients who are sedated, partially sedated, or intubated for prolonged periods develop exposure keratitis as a result of their eyelids remaining open and/or total body dehydration. Sedated patients often open their eyes but are unable to close them and have a poor blink response. Other patients cannot close their eyes properly due to severe chemosis.

Conventional methods for preventing exposure keratitis include applying ointment to the eyes or taping the eyelids shut. Both of these methods still commonly lead to corneal scarring which causes significant ocular morbidity from decreased visual acuity and often corneal ulceration. Another method for preventing exposure keratitis involves suturing the eyelids closed. Unfortunately, this method forces patients who regain consciousness to confront a dark world. Additionally, suturing the eyelids closed prevents doctors and nurses from being able to check a patient's pupils.

Other conventional methods for preventing exposure keratitis include the frequent use of artificial tears and the use of saran wrap to create a moisture chamber around a patient's eyes. However, patients with shallow orbits cannot tolerate the saran wrap and the saran wrap tends to erode their corneas. Thus, none of these conventional methods effectively prevent a patient from developing cornea damage.

OBJECTS AND ADVANTAGES OF THE INVENTION

In view of the above, it is a primary object of the present invention to provide a method and apparatus for effectively preventing a patient from developing exposure keratitis. It is another object of the invention to provide an apparatus for preventing exposure keratitis which allows a doctor or nurse to check the patient's pupils. It is a further object of the invention to provide an apparatus for preventing exposure keratitis which facilitates the placement of liquids in the patient's eyes.

These and other objects and advantages will become more apparent after consideration of the ensuing description and the accompanying drawings.

SUMMARY

The invention presents goggles for preventing the eyes of a patient from developing exposure keratitis. The goggles include first and second concave eyepieces for covering the eyes such that the first eyepiece forms a first chamber over a first one of the eyes and such that the second eyepiece forms a second chamber over a second one of the eyes. The first and second eyepieces have first and second holes, respectively.

The goggles also include a first flow regulator attached to the first eyepiece for regulating a fluid flow through the first hole. A second flow regulator is attached to the second eyepiece for regulating a fluid flow through the second hole. In the preferred embodiment, the first and second flow regulators are one-way valve assemblies which are inserted into the first and second holes, respectively. In a preferred method of use, liquids such as artificial tears are instilled in each chamber through the valve assemblies.

The goggles further include an adjustable nose strap connecting the eyepieces and an adjustable head strap connected to each eyepiece. In the preferred embodiment, the goggles additionally include first and second cushioning members, preferably ring-shaped air bladders, attached to the rims of the first and second eyepieces, respectively. The cushioning members prevent the patient from developing skin damage or pressure sores and establish a seal between the goggles and the patient's face.

DETAILED DESCRIPTION

Figure 1:
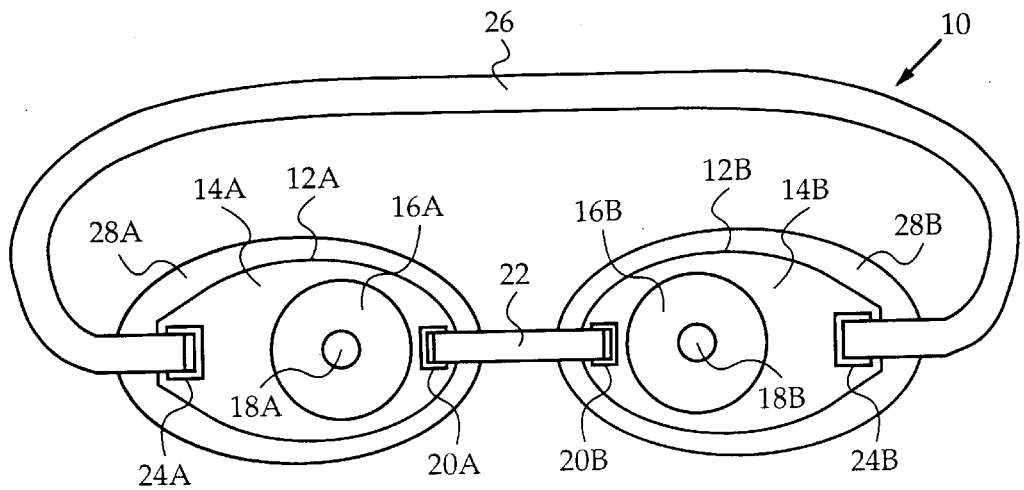
FIG. 1 is a schematic front view of goggles according to a preferred embodiment of the invention.
Figure 2:
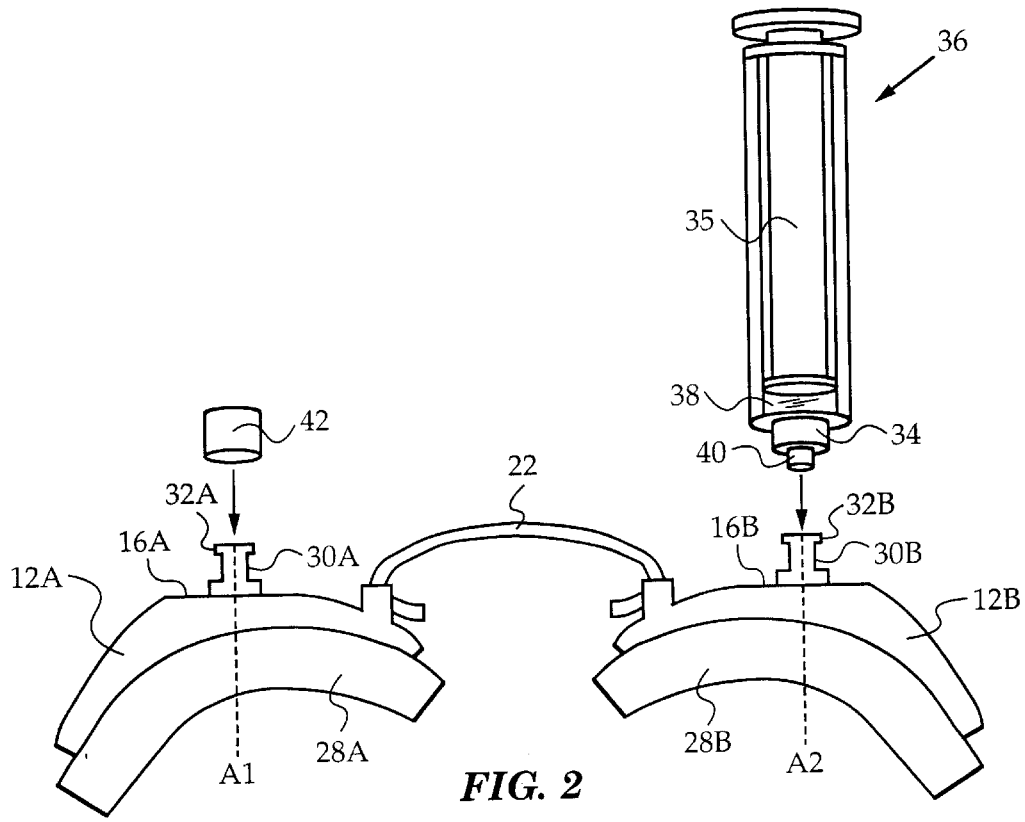
FIG. 2 is a schematic top view of the goggles of FIG. 1.

A preferred embodiment of the invention is illustrated in FIGS. 1–2. FIG. 1 shows a schematic front view of a pair of goggles 10 for preventing the dehydration of a patient's eyes and for facilitating the placement of liquids in the patient's eyes. Goggles 10 include a first concave eyepiece 12A and a second concave eyepiece 12B. Eyepieces 12A and 12B are designed to cover the patient's eyes such that eyepiece 12A forms a first chamber over a first eye of the patient and such that eyepiece 12B forms a second chamber over a second eye of the patient. Eyepiece 12A has a lens 16A which is connected to an eyepiece wall 14A for spacing lens 16A apart from the first eye. Similarly, eyepiece 12B has a lens 16B which is connected to an eyepiece wall 14B for spacing lens 16B apart from the second eye.

Goggles 10 also include two nose strap fasteners 20A and 20B which are attached to eyepieces 12A and 12B, respectively. The nose strap fasteners are preferably integrally formed with the eyepieces. An adjustable nose strap 22 is connected to fasteners 20A and 20B to connect eyepiece 12A to eyepiece 12B. Adjustable nose strap 22 is for adjusting the distance between the eyepieces. Goggles 10 also include two head strap fasteners 24A and 24B which are attached to eyepieces 12A and 12B, respectively. The head strap fasteners are preferably integrally formed with the eyepieces. An adjustable head strap 26 is connected to fasteners 24A and 24B. Head strap 26 is for securing goggles 10 to the patient's head.

As described thus far, goggles 10 resemble conventional swimming goggles whose manufacture and use is well known in the art. However, goggles 10 include several modifications which will now be described. A first cushioning member, such as ring-shaped air bladder 28A, is attached to the rim of eyepiece wall 14A. A second cushioning member, such as ring-shaped air bladder 28B, is attached to the rim of eyepiece wall 14A. Air bladders 28A and 28B establish seals with the face of the patient when goggles 10 are placed upon the patient. Air bladders 28A and 28B also prevent the patient from developing skin damage or pressure sores when wearing the goggles.

Ring-shaped air bladders are presently preferred in place of the foam rubber cushioning members used in conventional goggles. Conventional foam rubber often provides an insufficient cushion to prevent skin damage or pressure sores, particularly around the patient's medial canthal, orbital wall, and supraorbital ridge. Air bladders provide superior cushioning to prevent this damage. Additionally, foam rubber tends to collect bacteria which is harmful to the patient, while air bladders are more resistant to the collection of bacteria. The air bladders are preferably made of a material which resists the collection of bacteria and which is easily cleaned, such as a plastic.

Eyepiece 12A has a first hole 18A extending through lens 16A. Hole 18A is preferably located in the center of lens 16A. Similarly, eyepiece 12B has a second hole 18B extending through lens 16B. Hole 18B is preferably located in the center of lens 16B. Holes 18A and 18B may be drilled through lenses 16A and 16B, respectively, after the eyepieces are formed. Alternatively, the eyepieces may be formed such that holes 18A and 18B are present in lenses 16A and 16B.

Referring to FIG. 2, the first hole is sized to receive a first flow regulator, such as valve assembly 30A, for regulating a fluid flow through the first hole. Similarly, the second hole is sized to receive a second flow regulator, such as valve assembly 30B, for regulating a fluid flow through the second hole. Each valve assembly is preferably a one-way check valve assembly. Suitable valve assemblies are commercially available from many suppliers. The preferred embodiment uses check valve assemblies manufactured by Braun Medical Inc. of Bethlehem, Pa. These valve assemblies include valve plungers which are depressed to open the valve, permitting fluid flow through the valve assembly. Of course, many other types of valve assemblies may be used in alternative embodiments.

Valve assembly 30A is attached to lens 16A such that valve assembly 30A is in fluid communication with the first chamber formed by eyepiece 12A. Similarly, valve assembly 30B is attached to lens 16B such that valve assembly 30B is in fluid communication with the second chamber formed by eyepiece 12B. In the preferred embodiment, valve assemblies 30A and 30B are attached to lenses 16A and 16B by press fitting valve assemblies 30A and 30B into the first and second holes, respectively. Alternatively, the valve assemblies may be adhesively bonded to the lenses, screwed into the lenses, or snap fit to the lenses. Each valve assembly is preferably attached to a respective lens such that the inserted end of the valve assembly is substantially flush with the inner surface of the lens. This prevents the valve assembly from contacting the patient's eye when the goggles are placed upon the patient.

Valve assembly 30A includes a valve body having locking ears 32A and valve assembly 30B includes a valve body having locking ears 32B. Each valve body has a central bore for receiving a nozzle 40 of a fluid container, such as syringe 36. Each set of locking ears is designed to screw into an internally threaded collar 34 of syringe 36 such that nozzle 40 is received in the central bore. Such luer fittings are well known in the art and are presently preferred due to their predominant use in the medical field. However, those skilled in the art will recognize that there are many other methods for placing a container in fluid communication with a valve assembly and the scope of the invention is not limited to this particular implementation.

The operation of the preferred embodiment is illustrated in FIGS. 1–2. Referring to FIG. 1, a preferred method for using goggles 10 to prevent the development of exposure keratitis in a patient includes the step of securing goggles 10 to the patient using head strap 26. Goggles 10 are secured such that eyepiece 12A forms a first chamber over the patient's first eye and such that eyepiece 12B forms a second chamber over the patient's second eye. Once secured to the patient, goggles 10 provide a barrier to environmental elements such as drafts, air conditioning, and ventilation systems, thereby preventing dehydration of tears from the patient's eyes.

Referring to FIG. 2, the goggles are also preferably secured such that ring-shaped air bladders 28A and 28B are sealed to the patient's face around the patient's orbital rims. Additionally, nose strap 22 is preferably adjusted such that the longitudinal axis A1 of valve assembly 30A intersects the pupil of the first eye and such that the longitudinal axis A2 of valve assembly 30B intersects the pupil of the second eye.

Once the goggles are secured to the patient, liquid is placed in each chamber to keep the eyes moist and prevent injury from dehydration. The liquid is preferably instilled in each chamber through valve assemblies 30A and 30B. The patient is preferably lying down when the liquid is instilled so that each of the patient's pupils is located directly below a respective valve assembly. This ensures that the liquid flows to the center of the cornea, thereby hydrating the cornea. In the preferred embodiment, the liquid placed in each chamber is artificial tears. Alternatively, glaucoma medications, antibiotics, or any other therapeutic liquids may also be instilled through the valve assemblies.

To instill the liquid, syringe 36 is filled with a volume of artificial tears 38. The volume is preferably in the range of 2.0 to 4.0 cc with a preferred value of 3.0 cc. Syringe 36 is then fitted to one of the valve assemblies, for example assembly 30B, by screwing locking ears 32B into collar 34 such that nozzle 40 is inserted into the central bore of valve assembly 30B. When the nozzle is inserted, it depresses the valve plunger of assembly 30B so that syringe 36 is in fluid communication with the chamber formed by eyepiece 12B.

The artificial tears are then instilled in the chamber by depressing a plunger 35 of syringe 36. A similar procedure is used to instill liquid in the chamber formed by eyepiece 12A. After doses of artificial tears are placed in each chamber, the valve assemblies are preferably capped. Each valve assembly preferably includes an internally threaded cap 42 for placing on the valve assembly. Commercially available valve assemblies typically include caps suitable for this purpose. The artificial tears are preferably placed in each chamber about four times per day to ensure that the patient's corneas remain hydrated.

SUMMARY, RAMIFICATIONS, AND SCOPE

The goggles of the present invention have several advantages over conventional methods for preventing exposure keratitis. In particular, the goggles provide superior protection against exposure keratitis without necessitating the taping or suturing of a patient's eyelids. Thus, the goggles allow the patient's doctor or nurse to check the patient's pupils.

The goggles also allow the patient to retain partial vision during periods of consciousness. It is anticipated that the goggles of the present invention will be used on patients who are in surgery, intensive care units, or any other setting in which the patients risk corneal exposure.

It will be clear to one skilled in the art that the preferred embodiment described above may be altered in many ways without departing from the scope of the invention. For example, the flow regulators of the preferred embodiment comprise one way check valve assemblies which are attached to the eyepieces and adapted to receive a syringe. However, alternative embodiments include many other types of flow regulators. In one alternative embodiment, the flow regulators are simply plugs for plugging the holes in the lenses. The plugs are removed to dispense liquid into each goggle chamber and subsequently replaced in the holes to seal the chamber.

In another embodiment, the flow regulators are tubes attached to the eyepieces. Each tube has a cap which is removed to dispense liquid into a goggle chamber. The cap is then replaced to seal the chamber. Additionally, each flow regulator need not be a part which is manufactured separately from the lens. It is anticipated that the flow regulators may be integrally formed with the lenses. Further, liquid may be instilled in each goggle chamber using any suitable liquid dispensing mechanism. A syringe is presently preferred for ease of use, but the scope of the invention is not limited to this embodiment.

The preferred embodiment includes a unitary head strap for securing the goggles to a patient. However, alternative embodiments include other mechanisms for securing the goggles to the patient. In one alternative embodiment, the goggles include L-shaped arms similar to the arms used in the frames of glasses or spectacles. The goggles are secured to the patient by placing the arms around the patients ears. In a similar embodiment, the goggles include two ears straps for strapping the goggles to the patient's ears.

Therefore, the scope of the invention should be determined by the following claims and their legal equivalents.

What is claimed is:

1. Goggles for preventing the eyes of a patient from developing exposure keratitis, the goggles comprising:
    a) first and second concave eyepieces for covering the eyes such that the first eyepiece forms a first chamber over a first one of the eyes and such that the second eyepiece forms a second chamber over a second one of the eyes, wherein the first and second eyepieces have first and second holes, respectively;
    b) a first flow regulator attached to the first eyepiece for regulating a first fluid flow through the first hole; and
    c) a second flow regulator attached to the second eyepiece for regulating a second fluid flow through the second hole.

2. The goggles of claim 1, wherein the first and second flow regulators comprise first and second one-way valve assemblies inserted into the first and second holes, respectively.

3. The goggles of claim 2, wherein the first and second holes are located in the center of the first and second eyepieces, respectively, such that when the goggles are placed upon the patient, the longitudinal axis of the first valve assembly intersects the pupil of the first eye and the longitudinal axis of the second valve assembly intersects the pupil of the second eye.

4. The goggles of claim 1, wherein each of the flow regulators includes:
    a) a central bore for receiving a nozzle of a fluid container; and
    b) locking ears for attaching the fluid container to the flow regulator.

5. The goggles of claim 1, further comprising first and second cushioning members attached to the rims of the first and second eyepieces, respectively.

6. The goggles of claim 5, wherein the cushioning members comprise ring-shaped air bladders.

7. The goggles of claim 1, further comprising an adjustable nose strap connecting the eyepieces.

8. The goggles of claim 1, further comprising an adjustable head strap connected to each eyepiece for securing the goggles to the patient's head.

9. A method for preventing the eyes of a patient from developing exposure keratitis, the method comprising the steps of:
    a) securing to the patient goggles having first and second concave eyepieces, wherein the goggles are secured to the patient such that the first eyepiece forms a first chamber over a first one of the eyes and such that the second eyepiece forms a second chamber over a second one of the eyes; and
    b) placing liquid in each chamber to keep the eyes moist.

10. The method of claim 9, wherein the goggles further include first and second ring-shaped air bladders attached to rims of the first and second eyepieces, respectively, and wherein the goggles are secured such that the ring-shaped air bladders are sealed to the patient's face around the patient's orbital rims.

11. The method of claim 9, wherein the first and second eyepieces have first and second holes, respectively, the goggles further include:
    i) a first one-way valve assembly inserted in the first hole for regulating a first fluid flow through the first hole; and
    ii) a second one-way valve assembly inserted in the second hole for regulating a second fluid flow through the second hole;

and wherein the step of placing liquid in each chamber comprises instilling the liquid through the valve assemblies.

12. The method of claim 11, wherein the step of instilling the liquid through the valve assemblies comprises fitting a fluid container to at least one of the valve assemblies.

13. The method of claim 11, wherein the goggles are secured to the patient such that the longitudinal axis of the first valve assembly intersects the pupil of the first eye and such that the longitudinal axis of the second valve assembly intersects the pupil of the second eye.

14. The method of claim 11, further comprising the step of capping the valve assemblies after instilling the liquid.

15. The method of claim 9, wherein the liquid comprises artificial tears.

\* \* \* \* \*